(12) United States Patent
Nakamura et al.

(10) Patent No.: US 9,128,393 B2
(45) Date of Patent: Sep. 8, 2015

(54) TRIPHENYLAMINE DERIVATIVE, AND CHARGE TRANSPORT MATERIAL AND ELECTROPHOTOGRAPHIC PHOTORECEPTOR USING THE SAME

(71) Applicant: TAKASAGO INTERNATIONAL CORPORATION, Tokyo (JP)

(72) Inventors: Junji Nakamura, Chigasaki (JP); Yuji Nakayama, Kamakura (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/156,114

(22) Filed: Jan. 15, 2014

(65) Prior Publication Data

US 2014/0213822 A1    Jul. 31, 2014

(30) Foreign Application Priority Data

Jan. 29, 2013  (JP) ................. 2013-014549

(51) Int. Cl.
| C07C 211/00 | (2006.01) |
| C09B 11/02 | (2006.01) |
| G03G 5/06 | (2006.01) |
| C07C 211/54 | (2006.01) |

(52) U.S. Cl.
CPC ............ *G03G 5/0614* (2013.01); *C07C 211/54* (2013.01); *G03G 5/0672* (2013.01)

(58) Field of Classification Search
CPC ...... C08K 5/18; C07C 205/38; C07C 211/54; G03G 5/0614; G03G 5/0672
See application file for complete search history.

(56) References Cited

U.S. PATENT DOCUMENTS

| 5,573,878 | A | * | 11/1996 | Hagiwara et al. .......... 430/58.15 |
| 5,910,610 | A | * | 6/1999 | Kobayashi et al. ............. 564/315 |
| 5,989,765 | A | | 11/1999 | Kobayashi et al. |
| 6,172,264 | B1 | | 1/2001 | Kobayashi et al. |
| 7,083,862 | B2 | | 8/2006 | Burn et al. |
| 7,276,299 | B2 | | 10/2007 | Burn et al. |
| 7,682,708 | B2 | | 3/2010 | Burn et al. |
| 2003/0134147 | A1 | | 7/2003 | Burn et al. |
| 2006/0252963 | A1 | | 11/2006 | Burn et al. |
| 2008/0004471 | A1 | | 1/2008 | Burn et al. |

FOREIGN PATENT DOCUMENTS

| JP | 6123154 A | 1/1986 |
| JP | 62151389 A | 7/1987 |
| JP | 8-295655 A | 11/1996 |
| JP | 9-34142 A | 2/1997 |
| JP | 2003-522202 A | 7/2003 |
| JP | 2004-252066 A | 9/2004 |
| JP | 2005-289877 A | 10/2005 |
| JP | 2008-63230 A | 3/2008 |
| JP | 2012-156519 A | 8/2012 |

OTHER PUBLICATIONS

European Patent Office, Communication dated May 23, 2014, issued in corresponding European application No. 13197748.0.

* cited by examiner

*Primary Examiner* — Clinton Brooks
(74) *Attorney, Agent, or Firm* — Sughrue Mion, PLLC

(57) ABSTRACT

Disclosed is a triphenylamine derivative represented by general formula (1):

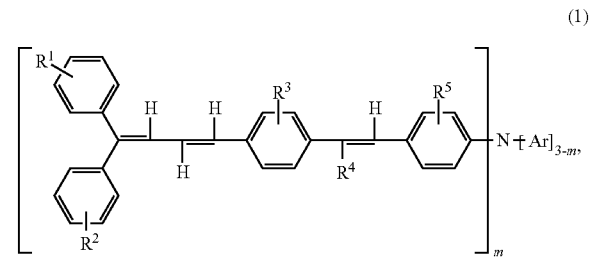

wherein $R^1$, $R^2$, $R^3$, and $R^5$ each independently represent a hydrogen atom, a substituted or unsubstituted alkyl group, a substituted or unsubstituted alkoxy group, or a substituted or unsubstituted phenyl group, $R^4$ represents a hydrogen atom, a substituted or unsubstituted alkyl group, or a substituted or unsubstituted phenyl group, Ar represents a substituted or unsubstituted phenyl group, and m represents an integer of 1 to 3.

10 Claims, No Drawings

TRIPHENYLAMINE DERIVATIVE, AND CHARGE TRANSPORT MATERIAL AND ELECTROPHOTOGRAPHIC PHOTORECEPTOR USING THE SAME

TECHNICAL FIELD

The present invention provides a triphenylamine derivative as an organic photoconductor for obtaining a highly responsive electrophotographic photoreceptor.

BACKGROUND ART

Recent advancement of information processing systems using the electrophotographic method is remarkable. In particular, laser printers and digital copiers which convert information to digital signals and record the information by using light have been remarkably improved in terms of their printing quality and reliability. Moreover, by being integrated with speed-enhancement technologies, these have been applied to laser printers and digital copiers capable of full-color printing.

As photoreceptors used for these laser printers, digital copiers, and the like employing the electrophotographic method, photoreceptors using organic photoreceptor materials (OPCs: organic photoconductors) have been generally and widely applied because of their costs, productivity, pollution free characteristics, and the like.

Recently, as the diameters of the photoreceptors get smaller (have shorter times taken from exposure to development) with the speedup or size-reduction of electrophotographic devices, high-speed response of charge transport materials for electrophotographic photoreceptors becomes increasingly important.

As the charge transport materials, tetraphenylbutadiene derivatives, hydrazone derivatives, triphenylamine derivatives, stilbene derivatives, and the like are used. Moreover, 4,4-diphenyl-1,3-butadienyl group-containing triphenylamine derivatives having longer conjugated systems (for example, 4,4',4"-tris(4'",4'"-diphenyl-1'",3'"-butadienyl) triphenylamine (Japanese Patent Application Publication No. Hei 8-295655)) than stilbene derivatives and the like exhibit high charge transport ability. Many patent applications have been filed also for butadienyl derivative (Japanese Patent Application Publication No. Hei 9-34142, Japanese Patent Application Publication No. 2004-252066, Japanese Patent Application Publication No. 2005-289877, and Japanese Patent Application Publication No. 2008-63230).

In addition, 4,4',4"-tris(4'"-(4""-phenyl-1'"",3""-butadienyl)styryl)triphenylamine), which is one of the organic compounds having longer conjugated systems, is reported to be used as a light-emitting dendrimer (International Application Japanese-Phase Publication No. 2003-522202 and Japanese Patent Application Publication Nu. 2012-156519).

In general, a charge transport layer is a solid solution film in which molecules of any of these low-molecular weight charge transport materials are dispersed in a binder resin and which is approximately 10 to 30 μm in thickness. In addition, for most electrophotographic photoreceptors, a bisphenol-based polycarbonate resin, a polyarylate resin, or a copolymer of any of these resins with another resin is used as the binder resin.

For forming the charge transport layer, the binder resin and the low-molecular weight charge transport material are dissolved in an organic solvent, and a film is formed therefrom. However, it cannot be said that conventional low-molecular weight charge transport materials are sufficiently soluble in the binder resin and the organic solvent. Moreover, although some of the low-molecular weight charge transport materials are soluble and films can be formed therefrom, the carrier mobilities of charge transport layers using the conventional low-molecular weight charge transport materials are not sufficiently high.

Hence, it cannot be said that an electrophotographic photoreceptor can be obtained which has excellent electrophotographic photoreceptor characteristics such as high sensitivity and low residual potential and moreover whose charge transport layer can be formed by a simple formation step and is in a stable state.

SUMMARY OF INVENTION

An object of the present invention is to provide a charge transport material which sufficiently satisfies characteristics conventionally desired for a charge transport material of an electrophotographic photoreceptor and which is highly responsive, i.e., has a high carrier mobility, and to provide an excellent electrophotographic photoreceptor using this material.

Moreover, another object of the present invention is to provide an intermediate useful for producing the charge transport material.

Under such a current situation, the present inventors have conducted intensive studies on various compounds. As a result, the present inventors have found that the above-described objects can be achieved by a novel triphenylamine derivative being represented by general formula (1) and having substituents with a diphenylbutadienylstyryl skeleton on one, two, or three phenyl groups of triphenylamine. Specifically, it has been found that the triphenylamine derivative of general formula (1) has a good solubility in a binder resin, does not undergo crystal formation and pinhole formation, and exhibits a high carrier mobility, and that a photoreceptor using this triphenylamine derivative is highly sensitive and has low residual potential. This finding has led to the completion of the present invention.

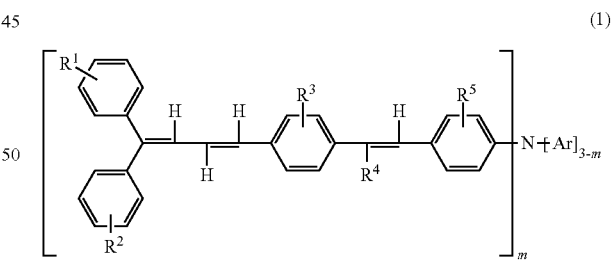

(1)

In the formula, $R^1$, $R^2$, $R^3$, and $R^5$ each independently represent a hydrogen atom, a substituted or unsubstituted alkyl group, a substituted or unsubstituted alkoxy group, or a substituted or unsubstituted phenyl group, $R^4$ represents a hydrogen atom, a substituted or unsubstituted alkyl group, or a substituted or unsubstituted phenyl group, Ar represents a substituted or unsubstituted phenyl group, and m represents an integer of 1 to 3.

Specifically, the present invention provides the following.

[1] A triphenylamine derivative represented by general formula (1):

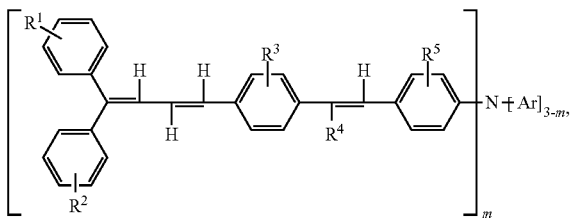

(1)

wherein $R^1$, $R^2$, $R^3$, and $R^5$ each independently represent a hydrogen atom, a substituted or unsubstituted alkyl group, a substituted or unsubstituted alkoxy group, or a substituted or unsubstituted phenyl group, $R^4$ represents a hydrogen atom, a substituted or unsubstituted alkyl group, or a substituted or unsubstituted phenyl group, Ar represents a substituted or unsubstituted phenyl group, and m represents an integer of 1 to 3.

[2] The triphenylamine derivative according to [1], wherein $R^1$, $R^2$, $R^3$, and $R^5$ each independently represent a hydrogen atom, a substituted or unsubstituted alkyl group having 1 to 6 carbon atoms, a substituted or unsubstituted alkoxy group having 1 to 6 carbon atoms, or a substituted or unsubstituted phenyl group.

[3] The triphenylamine derivative according to [1], which is represented by general formula (1'):

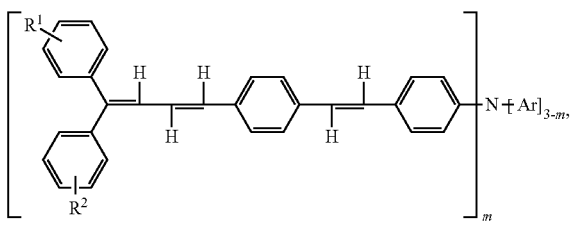

(1')

wherein $R^1$ and $R^2$ each independently represent a hydrogen atom or a substituted or unsubstituted alkyl group, Ar represents a substituted or unsubstituted phenyl group, and m represents an integer of 1 to 3.

[4] A charge transport material comprising the triphenylamine derivative according to any one of [1] to [3].

[5] An electrophotographic photoreceptor comprising the charge transport material according to [4].

[6] A halogen-containing compound represented by general formula (2):

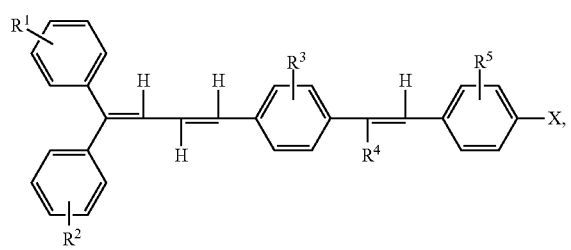

(2)

wherein $R^1$, $R^2$, $R^3$, $R^4$, and $R^5$ are the same as defined in formula (1), and X represents a chlorine atom, a bromine atom, or an iodine atom.

The triphenylamine derivative represented by general formula (1) of the present invention has good solubility in organic solvents and binder resins and a high carrier mobility, and hence is excellent as a charge transport material. In addition, the triphenylamine derivative is industrially excellent, because a photoreceptor layer formed therefrom is stable, and the triphenylamine derivative makes it possible to provide an electrophotographic photoreceptor having excellent electrophotographic characteristics.

DESCRIPTION OF EMBODIMENTS

Hereinafter, the present invention will be described in further detail.

A triphenylamine derivative of the present invention is represented by general formula (1):

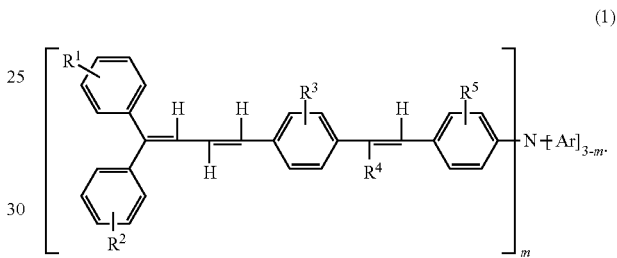

(1)

In general formula (1), $R^1$, $R^2$, $R^3$, and $R^5$ each independently represent a hydrogen atom, a substituted or unsubstituted alkyl group, a substituted or unsubstituted alkoxy group, or a substituted or unsubstituted phenyl group.

The alkyl group includes alkyl groups having 1 to 6 carbon atoms such as a methyl group, an ethyl group, a propyl group, and a butyl group. The alkyl group is preferably an alkyl group having 1 to 3 carbon atoms and further preferably a methyl group.

The alkoxy group includes alkoxy group having 1 to 6 carbon atoms such as a methoxy group, an ethoxy group, a propoxy group, and a butoxy group. The alkoxy group is preferably an alkoxy group having 1 to 3 carbon atoms and further preferably a methoxy group.

The substituents in the alkyl groups and the alkoxy groups include phenyl groups, halogen atoms, alkoxy groups, phenyloxy groups, and the like. The halogen atoms include fluorine atoms, chlorine atoms, bromine atoms, and iodine atoms. The alkoxy groups include alkoxy groups having 1 to 6 carbon atoms such as methoxy groups, ethoxy groups, propoxy groups, and butoxy groups.

The substituents in the phenyl group include alkyl groups having 1 to 6 carbon atoms, alkoxy groups having 1 to 6 carbon atoms, halogen atoms, and the like. Examples of the alkyl groups having 1 to 6 carbon atoms include methyl groups, ethyl groups, propyl groups, butyl groups, and the like. Examples of the alkoxy groups having 1 to 6 carbon atoms include methoxy groups, ethoxy groups, propoxy groups, butoxy groups, and the like. Examples of the halogen atoms include fluorine atoms, bromine atoms, chlorine atoms, and the like.

$R^4$ in general formula (1) represents a hydrogen atom, a substituted or unsubstituted alkyl group, or a substituted or unsubstituted phenyl group.

The substituted or unsubstituted alkyl group is the same as the substituted or unsubstituted alkyl group described for $R^1$, $R^2$, $R^3$, and $R^5$ above.

The substituted or unsubstituted phenyl group is the same as the substituted or unsubstituted phenyl group described for $R^1$, $R^2$, $R^3$, and $R^5$ above. Moreover, a substituent in the phenyl group may be a 4,4-diaryl-1,3-butadienyl group, a 2,2-diaryl-1-ethynyl group, or the like. Here, "aryl" is specifically the same as the substituted or unsubstituted phenyl group described for $R^1$, $R^2$, $R^3$, and $R^5$ above.

$R^1$ and $R^2$ are each particularly preferably a hydrogen atom or a methyl group, and $R^3$, $R^4$, and $R^5$ are each preferably a hydrogen atom.

Ar in general formula (1) represents a substituted or unsubstituted phenyl group.

The substituents in the phenyl group include alkyl groups having 1 to 6 carbon atoms, alkoxy groups having 1 to 6 carbon atoms, halogen atoms, and the like. Examples of the alkyl groups having 1 to 6 carbon atoms include methyl groups, ethyl groups, propyl groups, butyl groups, and the like. Examples of the alkoxy groups having 1 to 6 carbon atoms include methoxy groups, ethoxy groups, propoxy groups, butoxy groups, and the like. Examples of the halogen atoms include fluorine atoms, bromine atoms, chlorine atoms, and the like.

In general formula (1), m represents an integer of 1 to 3.

The triphenylamine derivative represented by general formula (1) is preferably represented by general formula (1'):

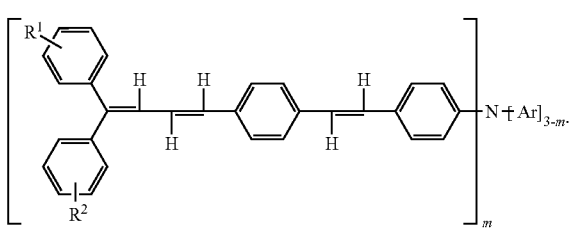

(1')

In general formula (1'), $R^1$ and $R^2$ each independently represent a hydrogen atom or a substituted or unsubstituted alkyl group. The substituted or unsubstituted alkyl group is the same as described above.

In general formula (1'), Ar represents a substituted or unsubstituted phenyl group. The substituted or unsubstituted phenyl group is the same as described above.

In general formula (1'), m represents an integer of 1 to 3.

The triphenylamine derivative represented by general formula (1) is further preferably represented by general formula (1"):

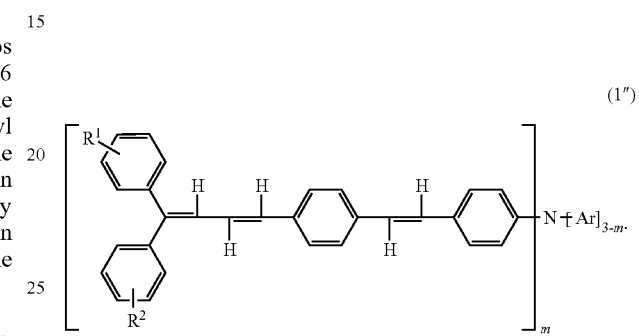

(1")

In general formula (1"), $R^1$ and $R^2$ each independently represent a hydrogen atom or a methyl group.

In general formula (1"), Ar represents a substituted or unsubstituted phenyl group. The substituted or unsubstituted phenyl group is the same as described above.

In general formula (1"), m represents an integer of 1 to 3.

The following compounds are preferred examples of general formula (1). However, the present invention is not limited to these compounds. In the following compounds, Et represents an ethyl group.

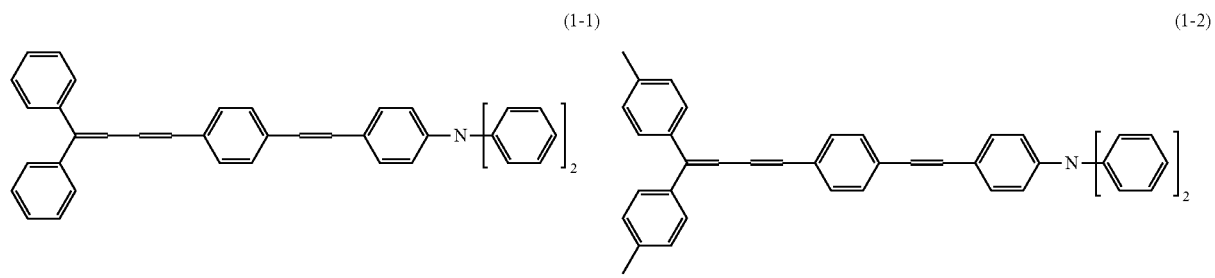

(1-1) (1-2)

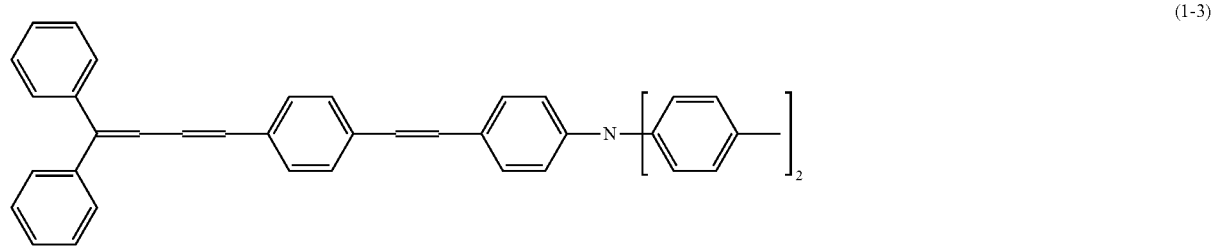

(1-3)

(1-4)
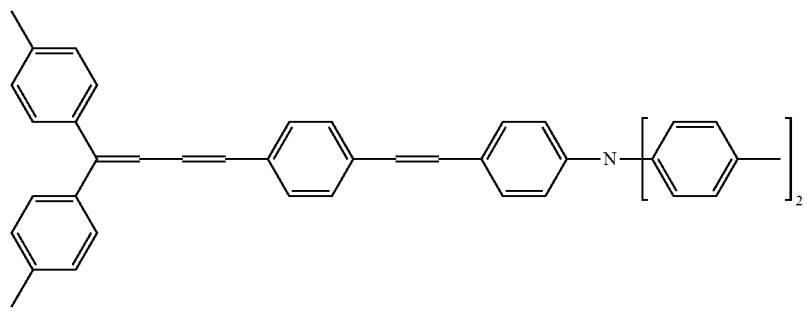
(1-5)
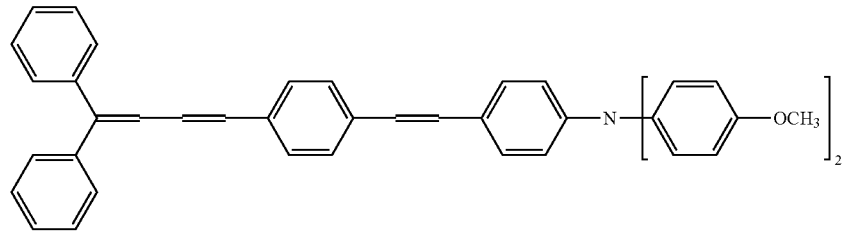
(1-6)
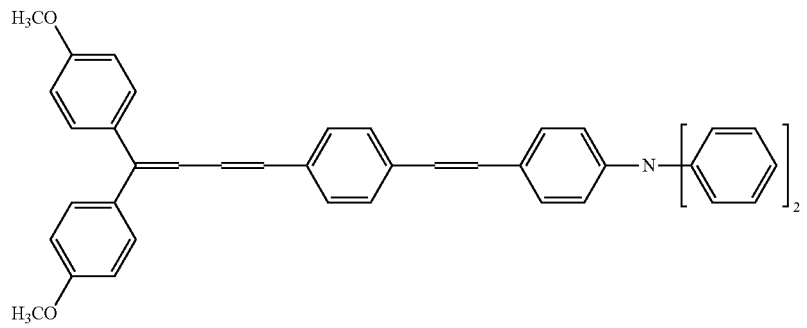
(1-7)　　　　　　　　　　(1-8)
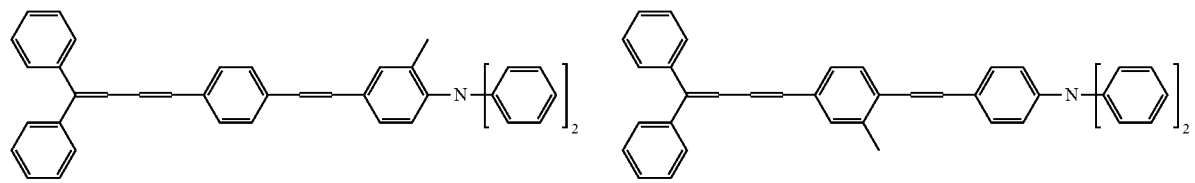
(1-9)　　　　　　　　　　(1-10)
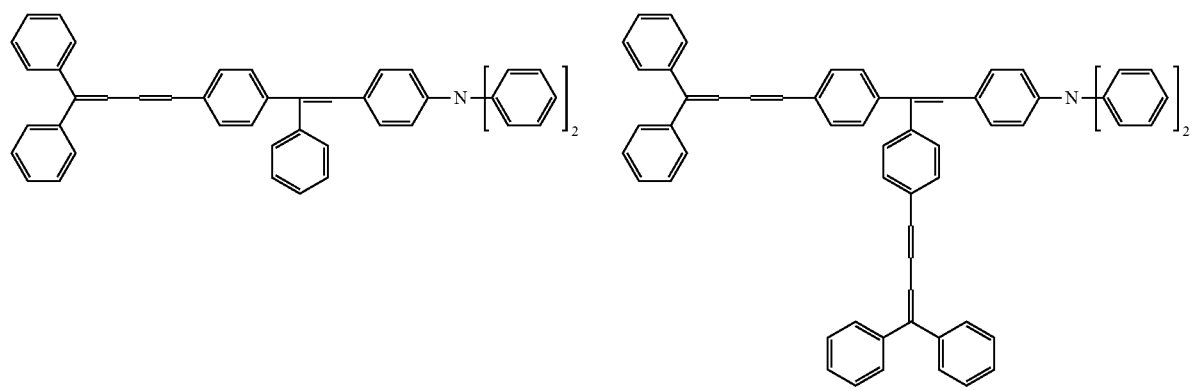

(1-11)
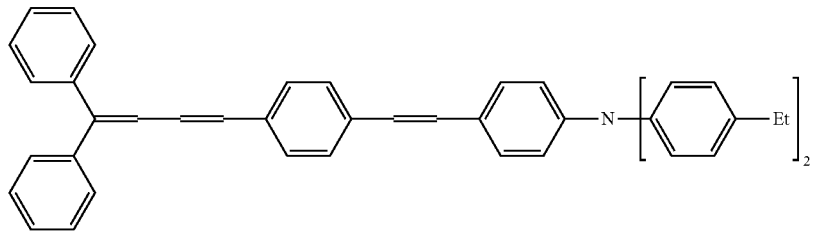
(1-12) (1-13)
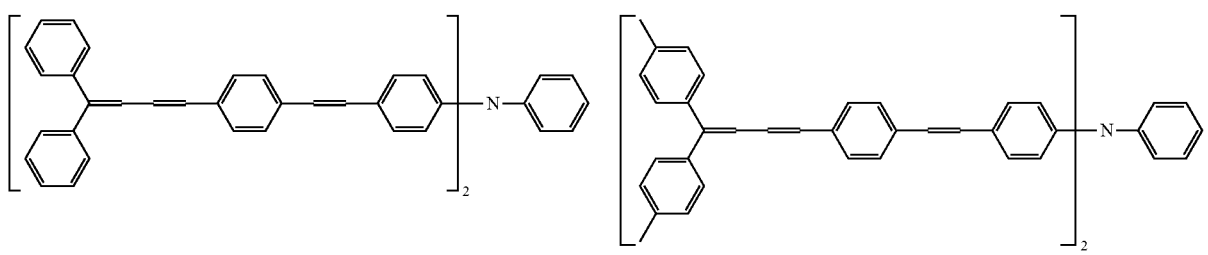
(1-14)
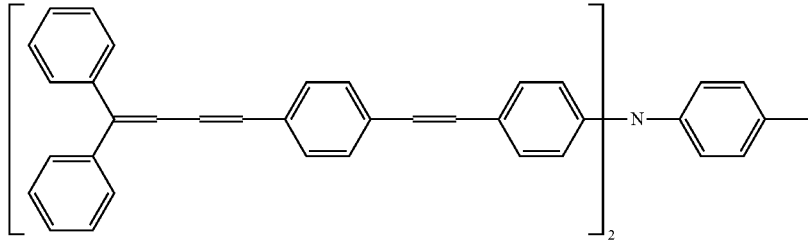
(1-15)
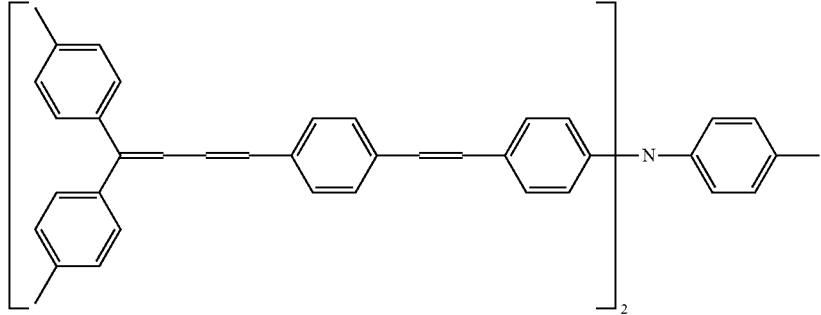
(1-16) (1-17)
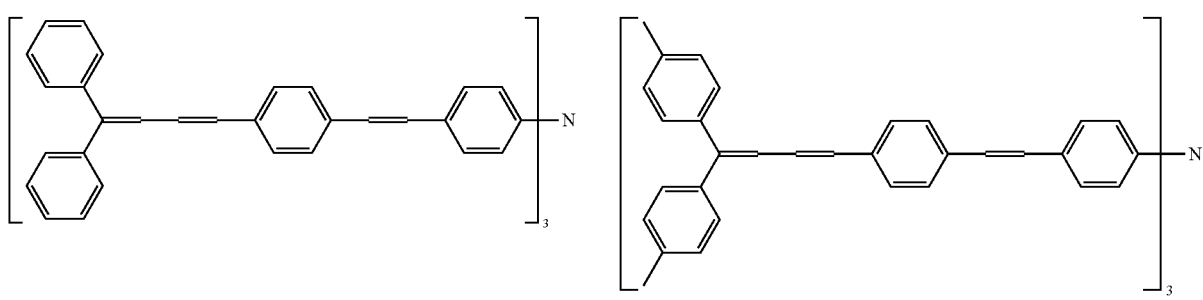

(1-18)

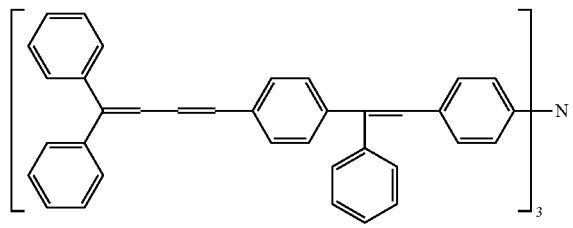

(1-19)

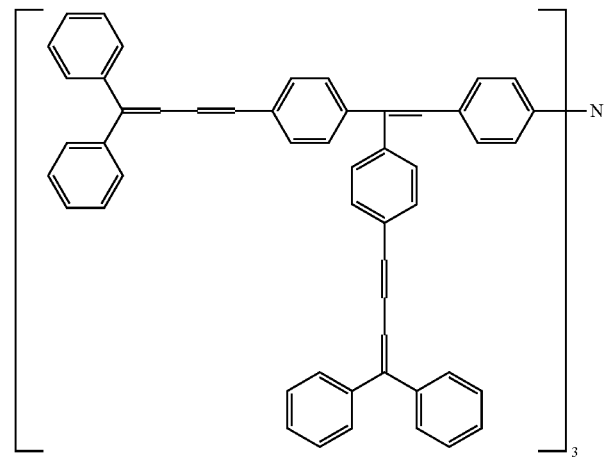

Of these compounds, Compounds (1-3), (1-4), (1-14), (1-16), and (1-17) are preferable.

The triphenylamine derivative represented by general formula (1) of the present invention can be synthesized via a halogen-containing compound represented by general formula (2) as an intermediate:

(2)

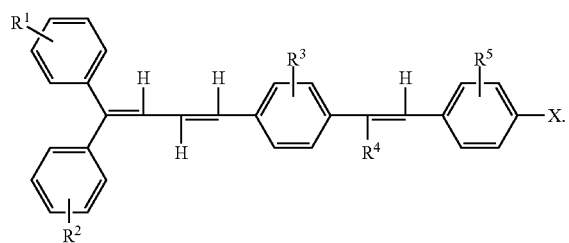

In general formula (2), $R^1$, $R^2$, $R^3$, $R^4$, and $R^5$ are the same as defined in general formula (1).

In general formula (2), X represents a chlorine atom, a bromine atom, or an iodine atom.

The following compounds are preferred examples of general formula (2). However, the present invention is not limited these compounds.

(2-1)

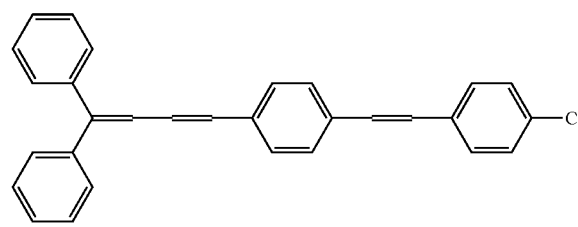

(2-2)

(2-3)

(2-4)

(2-5)

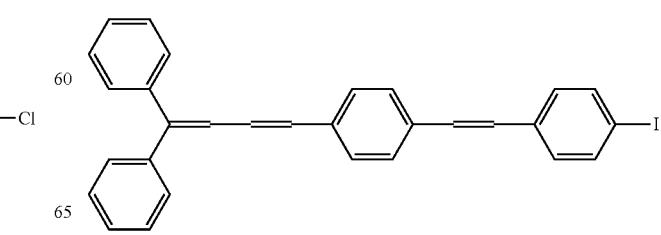

-continued (2-6)
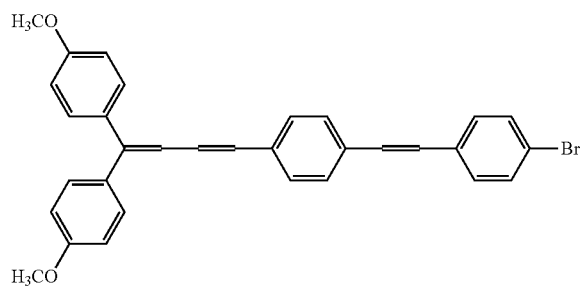

(2-7)
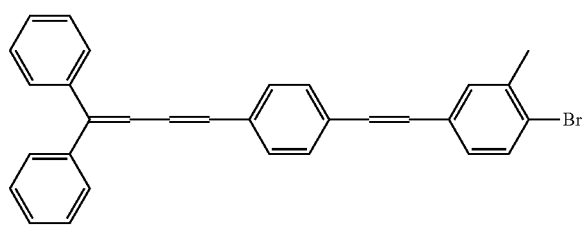

(2-8)
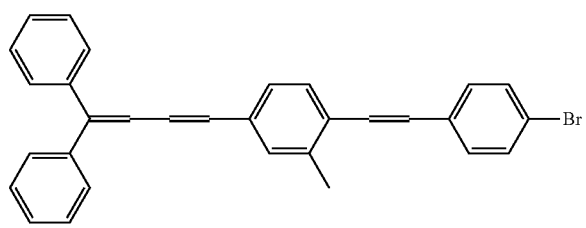

-continued (2-9)
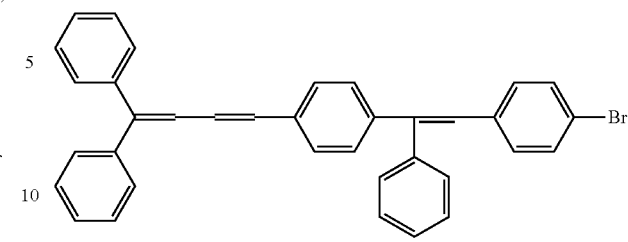

(2-10)
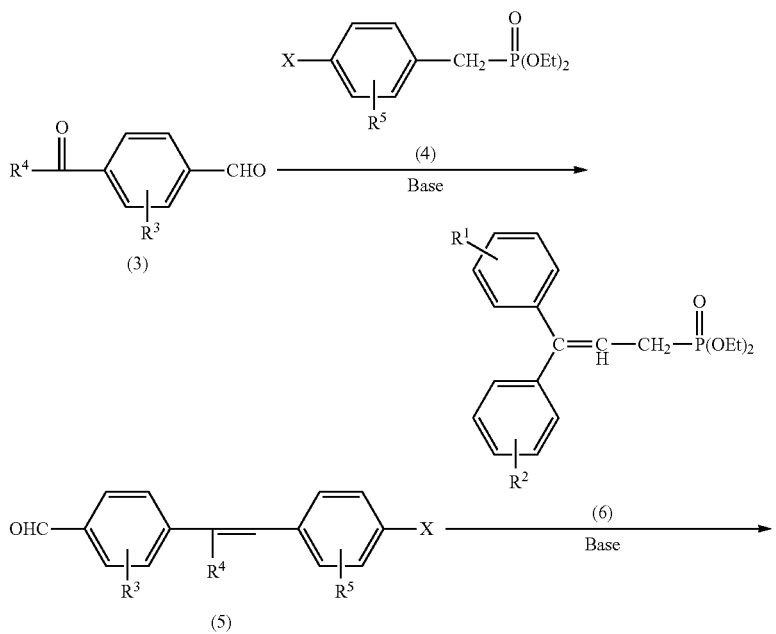

Of these compounds, Compounds (2-1), (2-2), (2-3), (2-4), and (2-5) are preferable.

Next, a method for synthesizing the triphenylamine derivative represented by general formula (1) of the present invention via the halogen-containing compound represented by general formula (2) as an intermediate is specifically described below. However, the present invention is not limited this method.

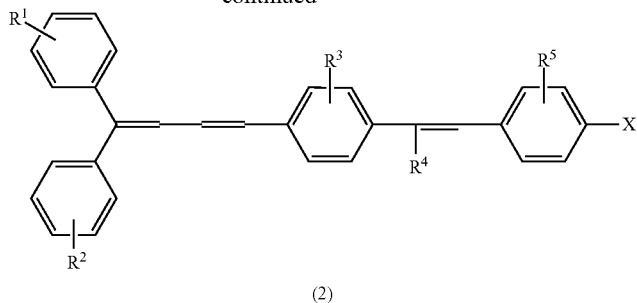

(2)

In scheme 1, Et represents an ethyl group.

For example, the target halogen-containing compound represented by general formula (2) of the present invention can be synthesized as follows. Specifically, a benzaldehyde derivative (3) and a para-halobenzylphosphonic acid ester derivative (Horner-Emmons reagent) (4) are reacted with each other in the presence of a base to synthesize a 4'-halostilbene-4-carbaldehyde (5). Then, 3,3-diarylallylphosphonic acid ester (Horner-Emmons reagent) (6) is reacted therewith in the presence of a base. The halogen-containing compound represented by general formula (2) is useful as an intermediate for producing the triphenylamine derivative represented by general formula (1) of the present invention.

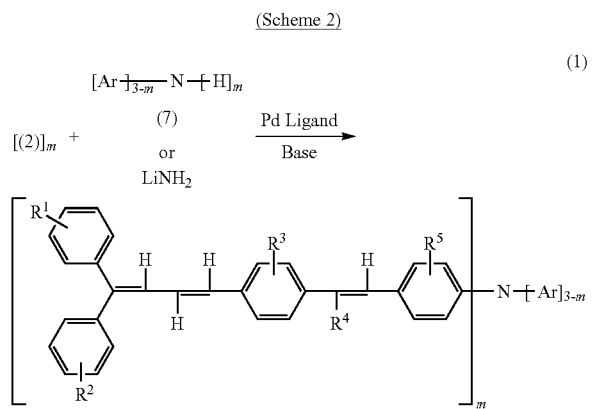

(Scheme 2)

Next, according to a method of Buchwald et al. (J. Org. Chem., 2000, 65, 5327), an aniline derivative (7) is reacted with the halogen-containing compound represented by general formula (2) in the presence of a palladium complex and a base or in the presence of a metal such as Pd, a phosphorus atom-containing ligand, and a base. Thus, the triphenylamine derivative represented by general formula (1) of the present invention can be synthesized.

Alternatively, according to another method of Buchwald et al. (Org. Lett. 2001, 3, 3417), the halogen-containing compound represented by general formula (2) is reacted with lithium amide ($LiNH_2$) in the presence of a palladium complex and a base or in the presence of a metal such as Pd, a phosphorus atom-containing ligand, and a base. Thus, the triphenylamine derivative represented by general formula (1) of the present invention can be synthesized.

Bases used in schemes 1 and 2 include sodium hydroxide, sodium amide, metal alkoxides such as sodium methoxide, sodium tert-butoxide, and potassium tert-butoxide, and the like.

Solvents used in schemes 1 and 2 include alcohols such as methanol and ethanol; ethers such as 1,2-dimethoxyethane, diethyl ether, tetrahydrofuran, and dioxane; hydrocarbons such as toluene and xylene; aprotic polar solvents such as dimethyl sulfoxide, N,N-dimethylformamide, N,N-dimethylacetamide, and N-methylpyrrolidone; mixtures of these solvents.

Palladium complexes usable in scheme 2 include $PdCl_2$, $Pd(OAc)_2$, $[PdCl(allyl)]_2$, $Pd_2(dba)_3$, and the like. Here, "Ac" represents an acetyl group, and "dba" represents dibenzylideneacetone.

The phosphorus atom-containing ligand includes triarylphosphine-based ligands such as triphenylphosphine and tri-o-tolylphosphine; trialkylphosphine-based ligands such as tri-t-butylphosphine and tricyclohexylphosphine; 2-phosphinobiphenyl-based ligands such as 2-(dicyclohexyl)phosphinobiphenyl, 2-(di-t-butylphosphino)biphenyl, 2-(dicyclohexylphosphino)-2',4',6'-tri-isopropyl-1,1'-biphenyl, and 2-(di-t-butylphosphino)-2'-(N,N-dimethylamino)biphenyl; olefin-substituted phosphine-based ligands such as 1,1-diphenyl-2-(dicyclohexylphosphino)propene and 1,1-diphenyl-2-(di-t-butylphosphino)propene; and cyclopropane ring-substituted phosphine-based ligands such as (di-t-butyl)(1-methyl-2,2-diphenylcyclopropyl)phosphine and (dicyclohexyl)(1-methyl-2,2-diphenylcyclopropyl)phosphine.

The triphenylamine derivative represented by general formula (1) of the present invention is useful as an electroconductive material for organic transistors, organic solar cells, and the like, and especially useful as a photoconductive material in a photoreceptor for a electrophotographic.

Specifically, the electrophotographic photoreceptor of the present invention may be a so-called function-separated type multilayer electrophotographic photoreceptors in which the functions of a photoreceptor layer are achieved separately by a charge generation layer and a charge transport layer provided on a conductive substrate, or a so-called single layer type electrophotographic photoreceptor in which a single photoreceptor layer containing a charge generation agent and a charge transport agent is provided on a conductive substrate.

For the function-separated type multilayer electrophotographic photoreceptor, the charge transport layer using the triphenylamine derivative represented by general formula (1) of the present invention as the charge transport agent can be formed as follows. Specifically, the triphenylamine derivative represented by general formula (1) of the present invention is directly vapor-deposited on a conductive substrate or on a charge generation layer, or a solution obtained by dissolving the triphenylamine derivative represented by general formula (1) of the present invention and a binder resin in an appropriate solvent is applied onto a conductive substrate or a charge generation layer, and then dried.

On the other hand, for the single layer type electrophotographic photoreceptor, the charge transport layer is formed as follows. Specifically, a solution obtained by dissolving or dispersing a charge generation agent, the triphenylamine derivative represented by general formula (1) of the present invention, and the like, as well as a binder resin, in an appropriate solvent is applied onto a conductive substrate, and then dried. Note that, if necessary, the single layer type electrophotographic photoreceptor may contain an electron transport material.

Examples of the binder resin include insulating polymers such as polyacrylates, polymethacrylates, polyamides, acrylic resins, acrylonitrile resins, methacrylic resins, vinyl chloride resins, vinyl acetate resins, phenolic resins, epoxy resins, polyesters, polyarylate (aromatic polyester) resins, alkyd resins, polycarbonates, polyurethanes, polystyrenes, and copolymers thereof. In addition to these insulating polymers, organic photoconductive polymers such as polyvinylcarbazole, polyvinylanthracene, and polyvinylene can also be used. Of these binder resins, it is particularly preferable to use a polyarylate resin or a polycarbonate.

Examples of polyarylate resins which can be preferably used include U series manufactured by UNITIKA LTD, and copolymerized polyarylate resins, and the like.

Polycarbonates which can be preferably used include polycarbonate resins of bisphenol A (2,2-bis(4-hydroxyphenyl)propane) (for example, Iupilon E series manufactured by Mitsubishi Gas Chemical Company, Inc.), polycarbonate resins of bisphenol (1,1-bis(4-hydroxyphenyl)cyclohexane) (for example, Panlite series manufactured by Teijin Chemicals Ltd., and Iupilon Z series manufactured by Mitsubishi Gas Chemical Company, Inc.), bisphenol/biphenol copolymerized polycarbonate resins disclosed in Japanese Patent Application Publication No. Hei 4-179961, and the like.

In addition to the above-described polycarbonates, polycarbonates disclosed in Japanese Patent Application Publication No. Hei 6-214412 or Japanese Patent Application Publication No. Hei 6-222581 can also be used.

Moreover, it is also possible to use polysiloxane-copolymerized polycarbonate resins, which are binder resins having excellent sliding properties and wear resistance, disclosed in Japanese Patent Application Publication No. Hei 5-297620 or Japanese Patent Application Publication No. Hei 5-158249.

Regarding the blending ratio of the binder resin and the triphenylamine derivative represented by general formula (1) of the present invention, the amount of all charge transport substances added, including the triphenylamine derivative represented by general formula (1) of the present invention, can be 1 to 1000 parts by weight, preferably 30 to 500 parts by weight, and further preferably 40 to 200 parts by weight relative to 100 parts by weight of the binder resin. In addition, relative to the total weight of all the charge transport substances, the triphenylamine derivative represented by general formula (1) of the present invention can be added in an amount of 0.1 to 100% by weight, preferably 1 to 100% by weight, further preferably 10 to 100% by weight.

The solvent used is not particularly limited, and organic solvents can be used. The organic solvents include alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethyl sulfoxide; ethers such as tetrahydrofuran, dioxane, and ethylene glycol dimethyl ether; esters such as ethyl acetate and methyl acetate; halogenated aliphatic hydrocarbons such as methylene chloride, chloroform, 1,2-dichloroethane, dichloroethylene, carbon tetrachloride, and trichloroethylene; aromatic compounds such as benzene, toluene, xylene, chlorobenzene, and dichlorobenzene; and the like. One of these solvents can be used alone, or a mixture of any ones of these can be used.

As the conductive substrate used for the photoreceptor of the present invention, a foil or a plate of a metal or an alloy of copper, aluminum, silver, iron, zinc, nickel, or the like is used in the form of a sheet or a drum. Alternatively, it is possible to use a conductive substrate obtained by vacuum-deposition or electrolytically plating such a metal onto a plastic film, cylinder, or the like, or a conductive substrate obtained by providing a layer of a conductive compound such as a conductive polymer, indium oxide, or tin oxide on a substrate such as a glass substrate, a paper substrate, or a plastic film by application or vapor-deposition.

The application can be conducted by a coating method such as a dip coating method, a spray coating method, a spinner coating method, a wire-bar coating method, a blade coating method, a roller coating method, or a curtain coating method.

For drying, a method of drying at room temperature followed by heat drying is preferable. The heat drying is preferably conducted at a temperature of 30 to 200° C. in the range from 5 minutes to 5 hours with or without an air stream.

Moreover, the electrophotographic photoreceptor of the present invention may contain charge transport materials other than the triphenylamine derivative represented by general formula (1) of the present invention, and also may contain various additives, if necessary. Examples of other charge transport materials include hydrazone compounds described in U.S. Pat. No. 4,150,987, Japanese Patent Application Publication No. Sho 61-23154, or the like; triphenylamine dimers described in Japanese Examined Patent Application Publication No. 58-32372 or the like; distyryl compounds described in U.S. Pat. No. 3,873,312 or the like; substituted or unsubstituted tetraphenylbutadiene-based compounds; α-phenylstilbenes; substituted or unsubstituted polyvinylcarbazoles; substituted or unsubstituted triphenylamines; substituted or unsubstituted triphenylmethanes; and the like.

Moreover, examples of other charge transport materials also include oxadiazole-based compounds such as 2,5-di(4-methylaminophenyl)-1,3,4-oxadiazole; organic polysilane compounds; pyrazoline-based compounds such as 1-phenyl-3-(p-dimethylaminophenyl)pyrazoline; nitrogen-containing cyclic compounds such as indole-based compounds, oxazole-based compounds, isoxazole-based compounds, thiazole-based compounds, thiadiazole-based compounds, imidazole-based compounds, pyrazole-based compounds, and triazole-based compounds; condensed polycyclic compounds; and the like.

One of these charge transport materials may be used alone, or two or more thereof may be used in combination. However, the present invention is not limited to these charge transport materials.

Examples of the various additives include plasticizers such as biphenylene-based compounds (for example, those disclosed in Japanese Patent Application Publication No. Hei 6-332206), m-terphenyl, and dibutyl phthalate; surface lubricants such as silicone oil, graft type silicone polymers, and various fluorocarbons; potential stabilizers such as dicyanovinyl compounds and carbazole derivatives; monophenol-based antioxidants such as 2-tert-butyl-4-methoxyphenol and 2,6-di-tert-butyl-4-methylphenol; bisphenol-based antioxidants; amine-based antioxidants such as 4-diazabicyclo[2,2,2]octane; salicylic acid-based antioxidants; tocopherols; and the like.

When the electrophotographic photoreceptor of the present invention is a function-separated type multilayer electrophotographic photoreceptor, the film thickness of the obtained charge transport layer is preferably 5 to 40 μm and more preferably 10 to 30 μm. The charge transport layer obtained as described above is electrically connected to a charge generation layer, and has functions of receiving carriers injected from the charge generation layer in the presence of an electric field and transporting these carriers across the charge transport layer to a surface opposite to the surface in contact with the charge generation layer. Here, the charge transport layer may be stacked above or below the charge generation layer, and the charge transport layer is preferably stacked above the charge generation layer. If necessary, a protective layer can be applied and formed on the thus prepared photoreceptor layer. In addition, an underlayer having a barrier function and an adhesive function may be provided between the conductive substrate and the photoreceptor layer. Materials for forming the underlayer include polyvinyl alcohol, nitrocellulose, casein, ethylene-acrylic acid copolymers, polyamides such as nylon, polyurethane, gelatin, aluminum oxide, and the like. The film thickness of the underlayer is preferably 0.1 to 5 μm and more preferably 0.5 to 3 μm.

For the charge generation layer, various organic pigments can be used.

The organic pigments include C. I. Pigment Blue 25 (Color Index: CI 21180); C. I. Pigment Red 41 (CI 21200); C. I. Acid Red 52 (CI 45100), C. I. Basic Red 3 (CI 45210); azo pigments such as azo pigments having a carbazole skeleton (Japanese Patent Application Publication No. Sho 53-95033), azo pigments having a distyrylbenzene skeleton (Japanese Patent Application Publication No. Sho 53-133445), azo pigments having a triphenylamine skeleton (Japanese Patent Application Publication No. Sho 53-132347), azo pigments having a dibenzothiophene skeleton (Japanese Patent Application Publication No. Sho 54-21728), azo pigments having an oxadiazole skeleton (Japanese Patent Application Publication No. Sho 54-12742), azo pigments having a fluorenone skeleton (Japanese Patent Application Publication No. Sho 54-22834), azo pigments having a bisstilbene skeleton (Japanese Patent Application Publication No. Sho 54-17733), azo pigments having a distyryloxadiazole skeleton (Japanese Patent Application Publication No. Sho 54-2129), azo pigments having a distyrylcarbazole skeleton (Japanese Patent Application Publication No. Sho 54-14967), and azo pigments having a benzanthrone skeleton; and the like. The organic pigments also include phthalocyanine-based pigments such as C. I. Pigment Blue 16 (CI 74100), Y-type oxotitanium phthalocyanine (Japanese Patent Application Publication No. Sho 64-17066), A(β)-type oxotitanium phthalocyanine, B(α)-type oxotitanium phthalocyanine, I-type oxotitanium phthalocyanine (Japanese Patent Application Publication No. Hei 11-21466), II-type chlorogallium phthalocyanine (Iijima et al., The 67th Annual Spring Meeting of The Chemical Society of Japan, 1B4, 04 (1994)), V-type hydroxygallium phthalocyanine (Daimon et al., The 67th Annual Spring Meeting of The Chemical Society of Japan, 1B4, 05 (1994)), and X-type metal-free phthalocyanine U.S. Pat. No. 3,816,118); indigo-based pigments such as C. I. Vat Brown 5 (CI 73410) and C. I. Vat Dye (CI 73030); perylene pigments such as Algo scarlet B (manufactured by Bayer AG) and Indanthrene scarlet R (manufactured by Bayer AG); and the like. Note that one of these materials may be used alone, or two or more thereof may be used in combination.

Moreover, inorganic pigments such as selenium, selenium-tellurium, cadmium sulfide, and α-silicon can also be used.

In the above-described manner, an electrophotographic photoreceptor containing the triphenylamine derivative represented by general formula (1) of the present invention can be obtained.

EXAMPLES

The present invention will be described in further detail below with reference to Examples. However, the present invention is not limited these examples. Note that measuring apparatuses and measurement conditions employed in Synthesis Examples were as follows:
(1) $^1$H-NMR apparatus: DRX-500 apparatus (500 MHz) manufactured by Bruker Corporation,
Internal standard substance: tetramethylsilane,
Measured in deuterated chloroform.
(2) Mass spectrometer: Shimadzu LCMS-IT-TOF (manufactured by Shimadzu Corporation).

Example 1

Synthesis of Compound (2-1) (4-(4'-(4",4"-diphenyl-1",3"-butadienyl)styryl)chlorobenzene)

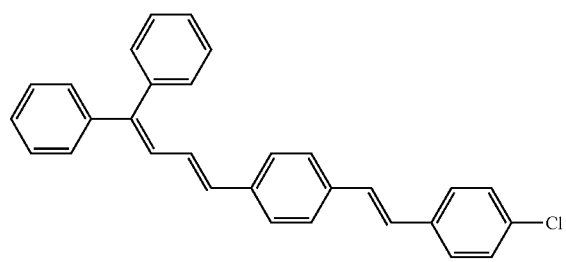 [SMILES: Clc1ccc(/C=C/c2ccc(/C=C/C=C(c3ccccc3)c3ccccc3)cc2)cc1]

To 64.4 g (0.4 mol) of p-chlorobenzyl chloride, 86.4 g (0.52 mol) of triethyl phosphite was added, followed by heating under reflux for 5 hours. The excess triethyl phosphite was removed under reduced pressure to obtain 108.6 g of a colorless liquid. In 800 ml of tetrahydrofuran, 26.3 g (0.1 mol) of the colorless liquid was dissolved, and further 67.1 g (0.5 mol) of terephthalaldehyde was added thereto. In a nitrogen atmosphere, 12.3 g (0.11 mol) of potassium tert-butoxide was added thereto, followed by stirring for further 3 hours. After extraction with toluene, the extract was washed with water, and then concentrated. Impurities were removed by silica gel column chromatography to obtain 8.0 g of 4-chlorostyrylbenzaldehyde as a white solid. The yield was 33%.

In 50 ml of tetrahydrofuran, 5.1 g (21 mmol) of the obtained 4-chlorostyrylbenzaldehyde was dissolved, and then 6.6 g (20 mmol) of diethyl 3,3-diphenylpropenylphosphonate was added thereto. In a nitrogen atmosphere, 2.5 g (22 mmol) of potassium tert-butoxide was added thereto, followed by stirring for further 3 hours. After extraction with toluene, the extract was washed with water, followed by recrystallization to obtain 6.1 g of a yellow solid (Compound (2-1)). The yield was 73%.

1H NMR (CDCl$_3$, δ): 6.73 (d, J=15.4 Hz, 1H), 6.87-6.94 (m, 2H), 7.00 (d, J=16.5 Hz, 1H), 7.03 (d, J=16.5 Hz, 1H), 7.25-7.32 (m, 11H), 7.38-7.45 (m, 7H)

Mass spectrometry ([M]+): found m/z 418.1465 [C30H23Cl]+ (calculated; 418.1468, −4.30 ppm)

Melting point: 173-174° C.

Example 2

Synthesis of Compound (2-2) (4-(4'-(4",4"-bis(4'''-methylphenyl)-1",3"-butadienyl)styryl)chlorobenzene)

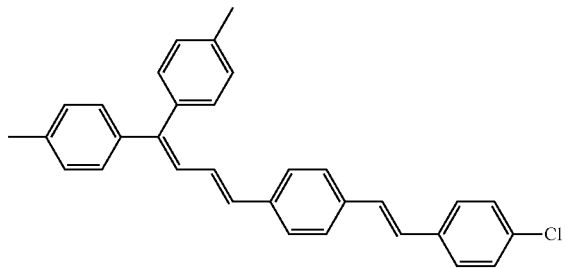 [SMILES: Cc1ccc(C(=C/C=C/c2ccc(/C=C/c3ccc(Cl)cc3)cc2)c2ccc(C)cc2)cc1]

In 50 ml of tetrahydrofuran, 5.1 g (21 mmol) of the 4-chlorostyrylbenzaldehyde obtained by the method of Example 1 was dissolved, and further 7.2 g (20 mmol) of diethyl 3,3-di-(4-dimethylphenyl)propenylphosphonate was added thereto. In a nitrogen atmosphere, 2.5 g (22 mmol) of potassium tert-butoxide was added thereto, followed by stirring for further 3 hours. After extraction with toluene, the extract was washed with water, followed by recrystallization to obtain 7.3 g of a yellow solid (Compound (2-2)). The yield was 82%.

1H NMR (CDCl$_3$, δ): 2.34 (s, 3H), 2.43 (s, 3H), 6.69 (d, J=15.4 Hz, 1H), 6.82 (d, J=11.1 Hz, 1H), 6.94 (dd, J=11.1, 15.4 Hz, 1H), 6.97 (d, J=16.4 Hz, 1H), 7.04 (d, J=16.4 Hz, 1H), 7.09-7.11 (m, 2H), 7.16-7.24 (m, 6H), 7.28-7.31 (m, 4H), 7.38-7.42 (m, 4H)

Mass spectrometry ([M]+): found m/z 446.1812 [C32H27Cl]+ (calculated; 446.1796, +3.59 ppm)

Melting point: 187-189° C.

Example 3

Synthesis of Compound (1-3) (4-(4'-(4",4"-diphenyl-1",3"-butadienyl)styryl)phenylbis(4'''-methylphenyl)amine)

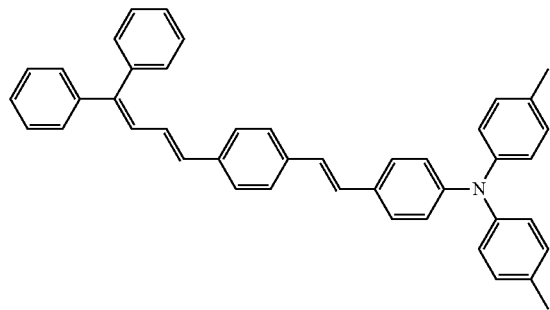 [SMILES: Cc1ccc(N(c2ccc(C)cc2)c2ccc(/C=C/c3ccc(/C=C/C=C(c4ccccc4)c4ccccc4)cc3)cc2)cc1]

In a nitrogen atmosphere, 3.6 g (8.5 mmol) of Compound (2-1) obtained in Example 1, 1.0 g (10.6 mmol) of sodium tert-butoxide, 1.8 g (8.9 mmol) of di-(p-tolyl)amine, 12.4 mg (0.040 mmol) of [PdCl(allyl)]$_2$, and 31.9 mg (0.096 mmol) of 1,1-diphenyl-2-(dicyclohexylphosphino)propene were added to 20 ml of xylene, followed by heating at 100° C. After stirring for 2 hours, water was added thereto, and further toluene was added for extraction to obtain an organic layer. The organic layer was washed with water and then concentrated. Impurities were removed by silica gel column chromatography to obtain 3.5 g of a yellow solid (Compound (1-3)). The yield was 72%.

1H NMR (CDCl$_3$, δ): 2.31 (s, 6H), 6.70-6.75 (m, 1H), 6.88-7.03 (m, 10H), 7.05-7.07 (m, 4H), 7.23-7.41 (m, 14H), 7.42-7.46 (m, 2H)

Mass spectrometry ([M]+): found m/z 579.2940 [C44H37N]+ (calculated; 579.2921, +3.28 ppm)

Melting point: 159° C.

Example 4

Synthesis of Compound (1-4) (4-(4'-(4",4"-bis(4'''-methylphenyl)-1",3"-butadienyl)styryl)phenylbis(4''''-methylphenyl)amine)

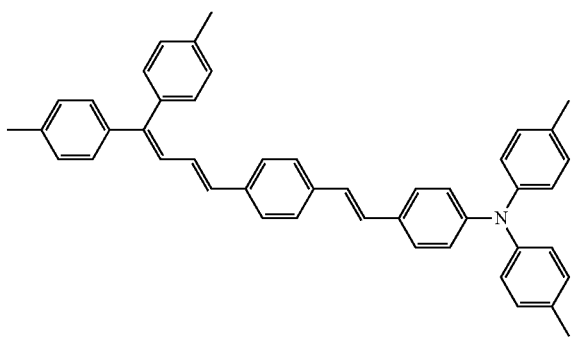

In a nitrogen atmosphere, 3.8 g (8.5 mmol) of Compound (2-2) obtained in Example 2, 1.0 g (10.6 mmol) of sodium tert-butoxide, 1.8 g (8.9 mmol) of di-(p-tolyl)amine, 12.4 mg (0.040 mmol) of [PdCl(allyl)]$_2$, and 31.9 mg (0.096 mmol) of 1,1-diphenyl-2-(dicyclohexylphosphino)propene were added to 30 ml of xylene, followed by heating at 100° C. After stirring for 2 hours, water was added thereto, and further toluene was added for extraction to obtain an organic layer. The organic layer was washed with water and then concentrated. Impurities were removed by silica gel column chromatography to obtain 0.5 g of a yellow solid (Compound (1-4)). The yield was 26%.

1H NMR (CDCl$_3$, δ): 2.31 (s, 6H), 2.34 (s, 3H), 2.43 (s, 3H), 6.69 (d, J=15.3 Hz, 1H), 6.82 (d, J=11.1 Hz, 1H), 6.91-6.95 (m, 2H), 6.97-7.02 (m, 7H), 7.04-7.07 (m, 4H), 7.08-7.11 (m, 2H), 7.15-7.24 (m, 6H), 7.27 (d, J=8.4 Hz, 2H), 7.31-7.33 (m, 2H), 7.37 (d, J=8.4 Hz, 2H)

Mass spectrometry ([M]+): found m/z 607.3216 [C46H41N]+ (calculated; 607.3234, −2.96 ppm)

Melting point: 165° C.

Example 5

Synthesis of Compound (1-14) (4,4'-bis((4"-(4'",4'"-diphenyl-1'",3'"-butadienyl) styryl)phenyl)(4""-methylphenyl)amine)

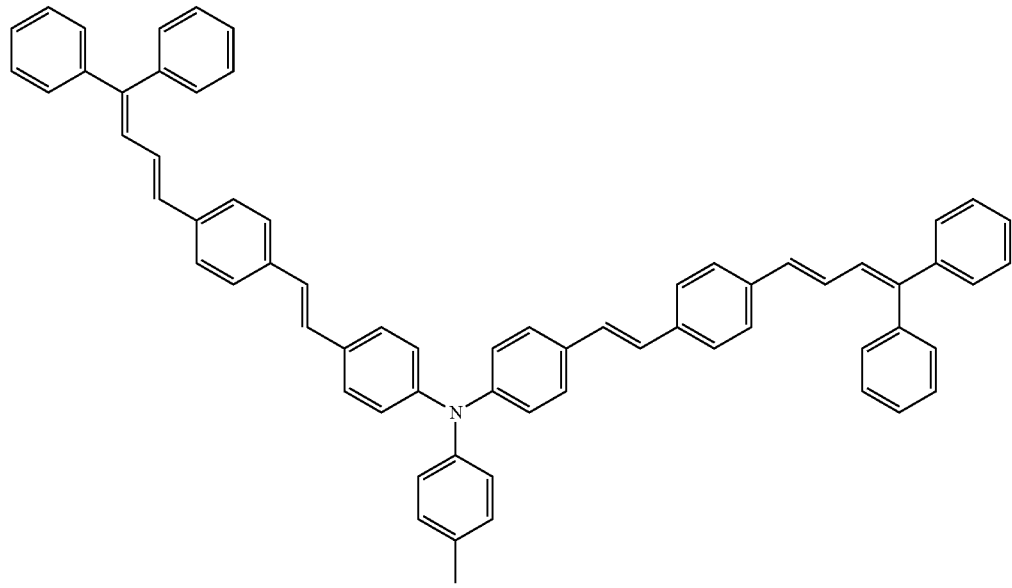 [SMILES: Cc1ccc(N(c2ccc(/C=C/c3ccc(/C=C/C=C(c4ccccc4)c4ccccc4)cc3)cc2)c2ccc(/C=C/c3ccc(/C=C/C=C(c4ccccc4)c4ccccc4)cc3)cc2)cc1]

In a nitrogen atmosphere, 5.0 g (12 mmol) of Compound (2-1) obtained in Example 1, 1.4 g (15 mmol) of sodium tert-butoxide, 0.6 g (6 mmol) of p-toluidine, 18 mg (0.048 mmol) of [PdCl(allyl)]$_2$, and 45 mg (0.12 mmol) of 1,1-diphenyl-2-(dicyclohexylphosphino)propene were added to 25 ml of xylene, followed by heating at 100° C. After stirring for 3 hours, water was added thereto, and further toluene was added for extraction to obtain an organic layer. The organic layer was washed with water and then concentrated. Impurities were removed by silica gel column chromatography to obtain 4.4 g of a yellow solid (Compound (1-14)). The yield was 85%.

1H NMR (CDCl$_3$, δ): 2.33 (s, 3H), 6.70-6.76 (m, 2H), 6.87-7.05 (m, 14H), 7.10 (d, J=8.1 Hz, 2H), 7.23-7.33 (m, 17H), 7.35-7.45 (m, 15H)

Mass spectrometry ([M]+): found m/z 871.4157 [C67H53N]+ (calculated; 871.4178, −2.41 ppm)

Melting point: 140° C.

Example 6

Synthesis of Compound (1-16) (4,4',4"-tris((4'''-(4'''', 4''''-diphenyl-1''', 3'''-butadienyl)styryl)phenyl) amine)

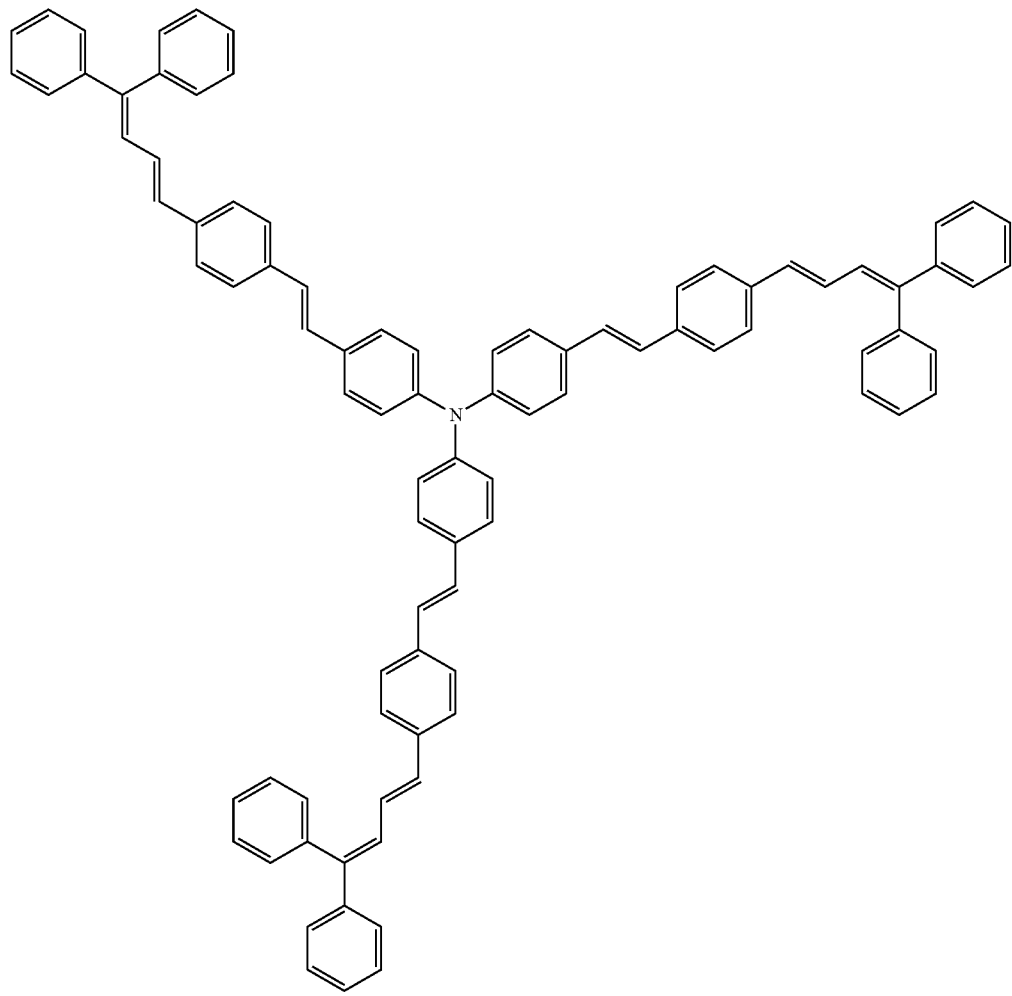 [SMILES: C(/C=C/c1ccc(/C=C/c2ccc(N(c3ccc(/C=C/c4ccc(/C=C/C=C(c5ccccc5)c5ccccc5)cc4)cc3)c3ccc(/C=C/c4ccc(/C=C/C=C(c5ccccc5)c5ccccc5)cc4)cc3)cc2)cc1)=C(c1ccccc1)c1ccccc1]

In a nitrogen atmosphere, 6.3 g (15 mmol) of Compound (2-1) obtained in Example 1, 1.4 g (15 mmol) of sodium tert-butoxide, 0.12 g (5 mmol) of lithium amide, 9.1 mg (0.025 mmol) of [PdCl(allyl)]$_2$, and 21 mg (0.060 mmol) of (di-t-butyl) (1-methyl-2,2-diphenylcyclopropyl)phosphine were added to 30 ml of xylene, followed by heating at 100° C. After stirring for 6 hours, water was added thereto, and further toluene was added for extraction to obtain an organic layer. The organic layer was washed with water and then concentrated. Impurities were removed by silica gel column chromatography to obtain 1.5 g of a yellow solid (Compound (1-16)). The yield was 25%.

1H NMR (CDCl$_3$, δ): 6.70-6.76 (m, 3H), 6.87-6.94 (m, 6H), 6.97 (d, J=16.3 Hz, 3H), 7.03 (d, J=16.3 Hz, 3H), 7.08 (d, J=8.7 Hz, 6H), 7.23-7.32 (m, 27H), 7.38-7.41 (m, 15H), 7.41-7.45 (m, 6H)

Mass spectrometry ([M]+): found m/z 1163.5437 [C90H69N]+ (calculated; 1163.5430, +0.60 ppm)

Melting point: 125° C.

Example 7

Synthesis of Compound (1-17) (4,4',4"-tris(4'"-(4"",4""-bis(4-methylphenyl)-1"",3""-butadienyl) styryl) phenyl)amine)

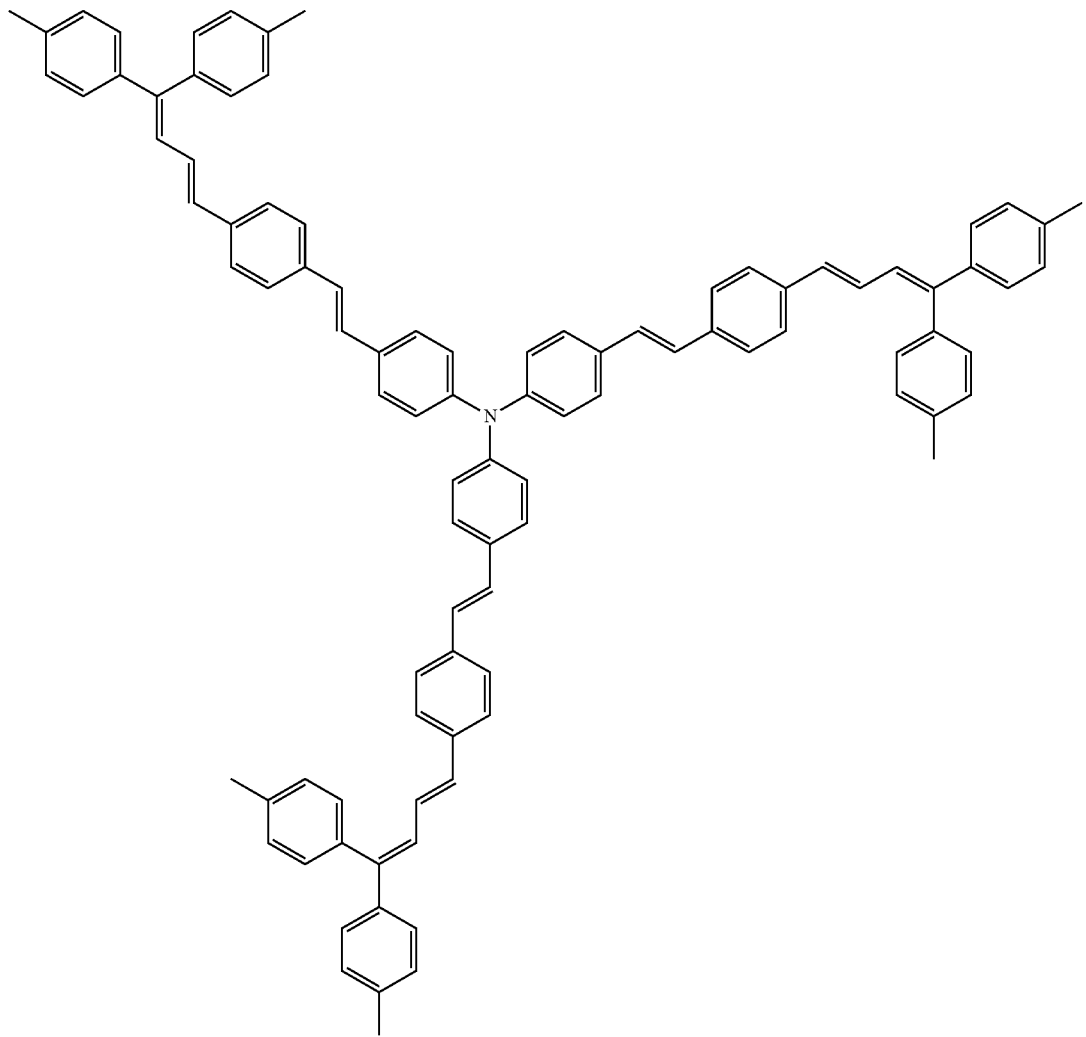

In a nitrogen atmosphere, 5.4 g (12 mmol) of Compound (2-2) obtained in Example 2, 1.4 g (15 mmol) of sodium tert-butoxide, 0.09 g (4 mmol) of lithium amide, 7.3 mg (0.02 mmol) of [PdCl(allyl)]$_2$, and 17 mg (0.048 mmol) of (di-t-butyl)(1-methyl-2,2-diphenylcyclopropyl)phosphine were added to 40 ml of xylene, followed by heating at 100° C. After stirring for 4 hours, water was added thereto, and further toluene was added for extraction to obtain an organic layer. The organic layer was washed with water and then concentrated. Impurities were removed by silica gel column chromatography to obtain 0.9 g of a yellow solid (Compound (1-17)). The yield was 36%.

1H NMR (CDCl$_3$, δ): 2.34 (s, 9H), 2.43 (s, 9H), 6.69 (d, J=15.3 Hz, 3H), 6.82 (d, J=11.1 Hz, 3H), 6.93 (dd, J=11.1, 15.4 Hz, 3H), 6.96 (d, J=16.2 Hz, 3H), 7.03 (d, J=16.2 Hz, 3H), 7.07-7.12 (m, 12H), 7.16-7.24 (m, 18H), 7.28 (d, J=8.4 Hz, 6H), 7.39 (d, J=8.7 Hz, 12H)

Mass spectrometry ([M]+): found m/z 1247.6356 [C96H81N]+ (calculated; 1247.6369, −0.99 ppm)

Melting point: 148° C.

Example 8

In 85 parts by weight of tetrahydrofuran, 15 parts by weight of a polycarbonate resin "TS-2020" (manufactured by Teijin Chemicals Ltd.) as a binder resin and 15 parts by weight of Compound (1-14) obtained in Example 5 were mixed and dissolved. The solution was applied with a doctor blade onto a sheet which had been obtained by vapor-deposition of aluminum on a polyethylene phthalate (PET) film, and dried at 80° C. for 3 hours to form a charge transport layer (thickness: 18 μm). No crystal formation was observed in the obtained charge transport layer.

A translucent gold electrode was vapor-deposited on this charge transport layer, and the charge carrier mobility was measured. The carrier mobility was measured by the time-of-flight method (Hiroaki Tanaka, Yasuhiro Yamaguchi, Yokoyama Masaaki: DENSHI SHASHIN GAKKAISHI (Electrophotography), 29, 366 (1990)) using, as the light source, a nitrogen gas laser with a pulse half width of 0.9 sec and a wavelength of 337 nm. Table 1 shows the results of the measurement at 25° C. and 25 V/μm.

Examples 9 and 10

Charge transport layers were formed in the same manner as in Example 8, except that Compound (1-16) obtained in Example 6 or Compound (1-17) obtained in Example 7 was used. Then, the charge carrier mobility thereof was measured. Table 1 shows the results.

Comparative Examples 1 and 2

Charge transport layers were formed in the same manner as in Example 8, except that Comparative Compound (1) or Comparative Compound (2) was used. Then, the charge carrier mobility thereof was measured. Table 1 shows the results.

Note that, Comparative Compound (1) was synthesized by the method described in Japanese Examined Patent Application Publication No. Hei 7-21646, and Comparative Compound (2) was synthesized by the method described in J. Org. Chem., 2000, 65, 5327.

Comparative Compound (1)

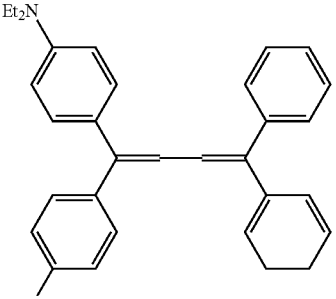

Comparative Compound (2)

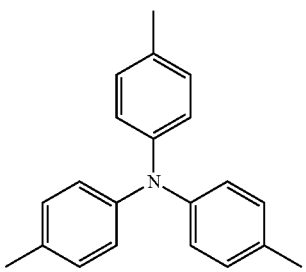

In Comparative Compound (1), Et represents an ethyl group.

TABLE 1

| | | Carrier mobility (cm$^2$/Vs) |
|---|---|---|
| Example 8 | Compound (1-14) | $4.2 \times 10^{-5}$ |
| Example 9 | Compound (1-16) | $5.6 \times 10^{-5}$ |
| Example 10 | Compound (1-17) | $5.5 \times 10^{-5}$ |
| Comparative Example 1 | Comparative Compound (1) | $0.3 \times 10^{-5}$ |
| Comparative Example 2 | Comparative Compound (2) | $0.7 \times 10^{-5}$ |

As is apparent from Table 1, it can be understood that the compounds of the present invention had higher carrier mobility and higher sensitivity than the compounds (Comparative Compound (1) and Comparative Compound (2)) which are generally and widely used as electrophotographic photoreceptors.

Example 11

To a binder solution obtained by dissolving 0.875 parts by weight of a butyral resin "BL-1" (manufactured by Sekisui Chemical Co., Ltd.) as a binder resin in 35.625 parts by weight of tetrahydrofuran, 1 part by weight of Y-type crystalline oxotitanium phthalocyanine "Y-TiOPc" (Sanyo Color Works, LTD.) was added, and dispersed therein by using a vibration mill with glass beads for 3 hours. The dispersion was applied onto a sheet, which had been obtained by vapor-deposition of aluminum on a polyethylene terephthalate (hereinafter abbreviated as PET) film, by using a wire bar (No. 03), and dried at 85° C. for 3 hours to form a charge generation layer.

In 85 parts by weight of tetrahydrofuran, 15 parts by weight of a polycarbonate resin "TS-2020" (manufactured by Teij in Chemicals Ltd.) as a binder resin and 15 parts by weight of Compound (1-4) obtained in Example 4 were mixed and dissolved. The solution was applied onto the charge generation layer with a doctor blade, and dried at 80° C. for 2 hours to form a charge transport layer (the thickness of the charge transport layer: 18 μm).

Photoreceptor characteristics of the thus obtained electrophotographic photoreceptor were measured by the static method using an Electrostatic Paper Analyzer "EPA-8300A" (manufactured by Kawaguchi Electric Works). Specifically, the electrophotographic photoreceptor was charged by a −6 kV corona discharge, and the surface potential $V_0$ (unit: −V) was measured. Then, this electrophotographic photoreceptor was held in a dark place for 5 seconds, and the surface potential $V_i$ (unit: −V) was measured. Then, the dark decay retention L/D ($V_i/V_0$ (unit: %)) was determined. After that, the electrophotographic photoreceptor was irradiated with laser light of 0.2 μW and 780 nm, and the amount of exposure required for reducing the surface potential $V_i$ to a half, i.e., the half decay exposure $E_{1/2}$ (mJ/cm$^2$) and the amount of exposure $E_{1/6}$ (mJ/cm$^2$) required for reducing the surface potential $V_i$ to ⅙ were determined. Subsequently, the surface residual potential $V_r$ (unit: −V) was measured after a 5 second irradiation. Table 2 shows the results.

Example 12

An electrophotographic photoreceptor was formed in the same manner as in Example 11, except that the charge transport layer was formed by using Compound (1-16) obtained in Example 6, and the photoreceptor characteristics were measured. Table 2 shows the results.

Comparative Examples 3 and 4

Electrophotographic photoreceptors were formed in the same manner as in Example 11, except that the charge transport layer was formed by using Comparative Compound (1) or Comparative Compound (3) ("CTC-191" manufactured by Takasago International Corporation), and the photoreceptor characteristics were measured. Table 2 shows the results.

Comparative Compound (3)

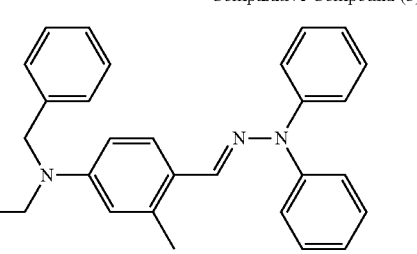

TABLE 2

|  |  | $V_0$ (-V) | $V_i$ (-V) | L/D (%) | $V_r$ (-V) | $E_{1/2}$ (mJ/cm$^2$) | $E_{1/6}$ (mJ/cm$^2$) |
|---|---|---|---|---|---|---|---|
| Example 11 | Compound (1-4) | 517 | 489 | 95 | 6 | 0.010 | 0.021 |
| Example 12 | Compound (1-16) | 495 | 440 | 89 | 2 | 0.010 | 0.021 |
| Comp. Ex. 3 | Comparative Compound (1) | 492 | 410 | 83 | 0 | 0.011 | 0.022 |
| Comp. Ex. 4 | Comparative Compound (3) | 528 | 462 | 88 | 91 | 0.016 | 0.150 |

As is apparent from Table 2, each of the electrophotographic photoreceptors using the compounds of the present invention had a higher dark decay retention (L/D) than the electrophotographic photoreceptor using Comparative Compound (1). In addition, each of the electrophotographic photoreceptors using the compounds of the present invention had a better sensitivity (i.e., had lower $E_{1/2}$ and $E_{1/6}$ values) and a lower residual potential ($V_r$) than the electrophotographic photoreceptor using Comparative Compound (3). Hence, it can be understood that the compound of the present invention provides an excellent electrophotographic photoreceptor.

INDUSTRIAL APPLICABILITY

The triphenylamine derivative represented by general formula (1) of the present invention is useful as a charge transport material. Moreover, the triphenylamine derivative is industrially excellent, because the triphenylamine derivative makes it possible to provide an electrophotographic photoreceptor having excellent electrical characteristics such as high carrier mobility, high sensitivity, and low residual potential.

The invention claimed is:

1. A triphenylamine derivative represented by general formula (1):

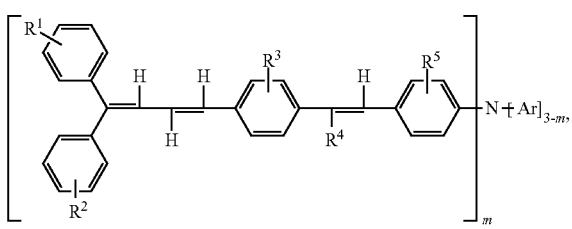

(1)

wherein $R^1$, $R^2$, $R^3$, and $R^5$ each independently represent a hydrogen atom, a substituted or unsubstituted alkyl group, a substituted or unsubstituted alkoxy group, or a substituted or unsubstituted phenyl group, $R^4$ represents a hydrogen atom, a substituted or unsubstituted alkyl group, or a substituted or unsubstituted phenyl group, Ar represents a substituted or unsubstituted phenyl group, and m represents an integer of 1 to 3.

2. The triphenylamine derivative according to claim 1, wherein $R^1$, $R^2$, $R^3$, and $R^5$ each independently represent a hydrogen atom, a substituted or unsubstituted alkyl group having 1 to 6 carbon atoms, a substituted or unsubstituted alkoxy group having 1 to 6 carbon atoms, or a substituted or unsubstituted phenyl group.

3. The triphenylamine derivative according to claim 1, which is represented by general formula (1'):

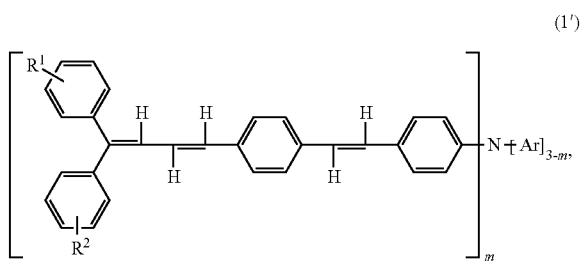

(1')

wherein $R^1$ and $R^2$ each independently represent a hydrogen atom or a substituted or unsubstituted alkyl group, Ar represents a substituted or unsubstituted phenyl group, and m represents an integer of 1 to 3.

4. A charge transport material comprising the triphenylamine derivative according to claim 1.

5. A charge transport material comprising the triphenylamine derivative according to claim 2.

6. A charge transport material comprising the triphenylamine derivative according to claim 3.

7. An electrophotographic photoreceptor comprising the charge transport material according to claim 4.

8. An electrophotographic photoreceptor comprising the charge transport material according to claim 5.

9. An electrophotographic photoreceptor comprising the charge transport material according to claim 6.

10. A halogen-containing compound represented by general formula (2):

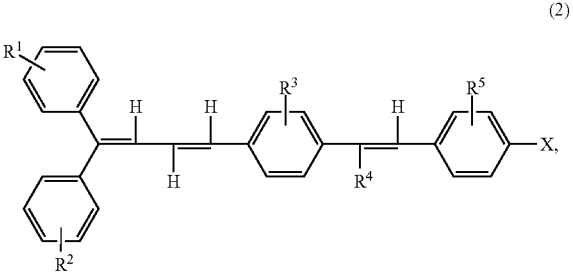

(2)

wherein $R^1$, $R^2$, $R^3$, $R^4$, and $R^5$ are the same as defined in formula (1), and X represents a chlorine atom, a bromine atom, or an iodine atom.

* * * * *